United States Patent
Maxwell et al.

(10) Patent No.: US 8,613,845 B2
(45) Date of Patent: Dec. 24, 2013

(54) SELF CONTAINED CAPILLARY ELECTROPHORESIS SYSTEM FOR INTERFACING WITH MASS SPECTROMETRY

(75) Inventors: Elizabeth Jane Maxwell, Vancouver (CA); Xuefei Zhong, Vancouver (CA); Hong Zhang, Burnaby (CA); David Da Yong Chen, Vancouver (CA)

(73) Assignee: The University of British Columbia, Vancouver, British Columbia (CA)

( * ) Notice: Subject to any disclaimer, the term of this patent is extended or adjusted under 35 U.S.C. 154(b) by 161 days.

(21) Appl. No.: 12/921,293

(22) PCT Filed: Mar. 6, 2009

(86) PCT No.: PCT/CA2009/000242
§ 371 (c)(1),
(2), (4) Date: Nov. 9, 2010

(87) PCT Pub. No.: WO2009/109037
PCT Pub. Date: Sep. 11, 2009

(65) Prior Publication Data
US 2011/0042216 A1 Feb. 24, 2011

Related U.S. Application Data

(60) Provisional application No. 61/064,485, filed on Mar. 7, 2008, provisional application No. 61/193,214, filed on Nov. 6, 2008.

(51) Int. Cl.
*G01N 27/453* (2006.01)
*H01J 49/04* (2006.01)

(52) U.S. Cl.
USPC .......................................... 204/601; 250/288

(58) Field of Classification Search
USPC .................... 204/601, 603, 451, 452; 250/288
See application file for complete search history.

(56) References Cited

U.S. PATENT DOCUMENTS 5,358,613 A * 10/1994 Schneider et al. ............ 204/453
5,423,964 A    6/1995 Smith et al.
(Continued)

FOREIGN PATENT DOCUMENTS

CN    1749749 A    3/2006
DE    4244474 A1   7/1994
(Continued)

OTHER PUBLICATIONS

Liu, C.C. et al., "Design, optimisation and evaluation of a sheath flow interface for automated capillary electrophoresis-electrospray-mass spectrometry," Electrophoresis 2005, 26, pp. 1366-1375.
(Continued)

*Primary Examiner* — Alex Noguerola
(74) *Attorney, Agent, or Firm* — Brooks Kushman P.C.

(57) ABSTRACT

A complete capillary electrophoresis (CE) system that is capable of providing a continuous flow of effluent at the exit of the flow-through outlet vial is provided. A self-contained capillary electrophoresis system with a flow-through outlet vial for interfacing with mass spectrometry includes a capillary having an upstream inlet end and a downstream terminus end; an electrically conductive hollow needle having an inner wall defining an internal tapered chamber, the internal tapered chamber dimensioned and configured to slidably accept the terminus end of the capillary, the capillary longitudinally inserted into and mounted within the internal tapered chamber to a distance whereby the terminus end of the capillary abuts the inner wall of the needle at the taper; and wherein a micro-reservoir is formed between the terminus end of the capillary and the downstream exit orifice.

44 Claims, 9 Drawing Sheets

(56) References Cited

U.S. PATENT DOCUMENTS

| | | | |
|---|---|---|---|
| 5,478,315 | A | 12/1995 | Brothers et al. |
| 5,788,166 | A | 8/1998 | Valaskovic et al. |
| 6,032,876 | A | 3/2000 | Bertsch et al. |
| 6,083,372 | A | 7/2000 | Grover et al. |
| 7,883,034 | B2 * | 2/2011 | Matsui et al. ............ 239/695 |
| 2003/0136680 | A1 | 7/2003 | Benner et al. |
| 2005/0061673 | A1 | 3/2005 | Presto Elgstoen et al. |
| 2005/0161329 | A1 | 7/2005 | Hutterer et al. |

FOREIGN PATENT DOCUMENTS

| | | |
|---|---|---|
| EP | 1635375 A1 | 3/2006 |
| JP | 06-174693 A | 6/1994 |
| WO | 9221138 A1 | 11/1992 |
| WO | 01/61338 A1 | 8/2001 |
| WO | 03061805 A1 | 7/2003 |

OTHER PUBLICATIONS

Moini, M., "Simplifying CE-MS Operation. 2. Interfacing Low-Flow Separation Techniques to Mass Spectrometry Using a Porous Tip," Analytical Chemistry, vol. 79, No. 11, Jun. 1, 2007, pp. 4241-4246.

Tseng, M.-C. et al., "A beveled tip sheath liquid interface for capillary electrophoresis-electrospray ionization-mass spectrometry," Electrophoresis Wiley-VCH Germany, v. 25, No. 13, pp. 2084-2089, 2004.

Wahl et al. "Attomole Level Capillary Electrophoresis-Mass Spectrometric Protein Analysis Using 5-μm-i.d. Capillaries", Analytical Chemistry 1992, vol. 64, p. 3194-3196.

Olivares et al. "On-Line Mass Spectrometric Detection for Capillary Zone Electrophoresis", Analytical Chemistry 1987, vol. 59, p. 1230-1232.

Petersson et al. "New Sheathless Interface for Coupling Capillary Electrophoresis to Electrospray Mass Spectrometry Evaluated by the Analysis of Fatty Acids and Prostaglandins", Journal of Chromatography A 1999, vol. 854, p. 141-154.

Pleasance et al. "Comparison of Liquid-Junction and Coaxial Interfaces for Capillary Electrophoresis-Mass Spectrometry with Application to Compounds of Concern on the Aquaculture Industry", Journal of Chromatography 1992, vol. 591, p. 325-339.

Kebarle et al. "From Ions in Solution to Ions in the Gas Phase the Mechanism of Electrospray Mass Spectrometry", Analytical Chemistry Nov. 15, 1993, vol. 65, No. 22, p. 972-986.

Chang et al. "Sheathless Capillary Electrophoresis/Electrospray Mass Spectrometry Using a Carbon-Coated Tapered Fused-Silica Capillary with a Beveled Edge", Anal. Chem. 2001, vol. 73, p. 5083-5087.

Dahlin et al. "Capillary Electrophoresis Coupled to Mass Spectrometry from a Polymer Modified Poly (Dimethylsiloxane) Microchip with an Integrated Graphite Electrospray Tip", Analyst 2005, vol. 130, p. 193-199.

Dole et al. "Molecular Beams of Macroions", The Journal of Chemical Physics Sep. 1, 1968, vol. 49, No. 5, p. 2240-2249.

Fang et al. "On-Line Time-of-Flight Mass Spectrometric Analysis of Peptides Separated by Capillary Electrophoresis", Anal. Chem. 1994, vol. 66, p. 3696-3701.

Figeys et al. "Protein Identification by Solid Phase Microextraction-Capillary Zone Electrophoresis-Microelectrospray Tandem Mass Spectrometry", Nature Biotechnology Nov. 1996, vol. 14, p. 1579-1583.

Iribarne et al. "On the Evaporation of Small Ions from Charged Droplets", The Journal of Chemical Physics Mar. 15, 1976, vol. 64, No. 6, p. 2287-2294.

Janini et al. "A Sheathless Nanoflow Electrospray Interface for On-Line Capillary Electrophoresis Mass Spectrometry", Anal. Chem. 2003, vol. 75, p. 1615-1619.

Bendahl et al. "A New Sheathless Electrospray Interface for Coupling of Capillary Electrophoresis to Ion-Trap Mass Spectrometry", Rapid Communication in Mass Spectrometry 2002, vol. 16, p. 2333-2340.

Cao et al. "A Novel Sheathless Interface for Capillary Electrophoresis/Electrospray Ionization Mass Spectrometry Using an In-Capillary Electrode", American Society for Mass Spectrometry 1997, vol. 8, p. 561-564.

Chang et al. "Sheathless Capillary Electrophoresis/Electrospray Mass Spectrometry Using a Carbon-COated Fused-Silica Capillary", Anal. Chem. 2000, vol. 72, p. 626-630.

Ramsey et al. "Capillary Electrophoresis/Electrospray Ionization Ion Trap Mass Spectrometry Using a Sheathless Interface", J. Microcolumn Separations 1995, vol. 7, No. 5, p. 461-469.

Kele et al. "Design and Performance of a Cheathless Capillary Electrophoresis/Mass Spectrometry Intereface by Combining Fused-Silica Capillaries with Gold-Coated Nanoelectrospray Tips", Rapid Communications in Mass Spectrometry 2005, vol. 19, p. 881-885.

Mazereeuw et al. "A Novel Sheathless and Electrodeless Microelectrospray Interface for the On-line Coupling of Capillary Zone Electrophoresis to Mass Spectrometry", Rapid Communications in Mass Spectrometry 1997, vol. 11, p. 981-986.

Moini "Design and Performance of a Universal Sheathless Capillary Electrophoresis to Mass Spectrometry Interface Using a Split-Flow Technique", Anal. Chem. 2001, vol. 73, p. 3497-3501.

Nilsson et al. "Gold-Coated Fused-Silica Sheathless Electrospray Emitters Based on Vapor-Deposited Titanium Adhesion Layers", Rapid Communications in Mass Spectrometry 2003, vol. 17, p. 1535-1540.

Nilsson et al. "A Simple and Robust Conductive Graphite Coating for Sheathless Electrospray Emitters Used in Capillary Electrophoresis/Mass Spectrometry", Rapid Communications in Mass Spectrometry 2001, vol. 15, p. 1997-2000.

Schmelzeisen-Redeker et al. "Desolvation of Ions and Molecules in Thermospray Mass Spectrometry", International Journal of Mass Spectrometry and Ion Process 1989, vol. 90, p. 139-150.

Severs et al. "Characterization of the Microdialysis Junction Interface for Capillary Electrophoresis/Microelectrospray Ionization Mass Spectrometry", Anal. Chem. 1997, vol. 69, p. 2154-2158.

Smith et al. "Improved Electrospray Ionization Interface for Capillary Zone Electrophoresis-Mass Soectrimetry", Anal. Chem. 1988, vol. 60, p. 1948-1952.

Tong et al. "Identification of Proteins in Complexes by Solid-Phase Microextraction/Multistep Elution/Capillary Electrophoresis/Tandem Mass Spectrometry", Anal. Chem. 1999, vol. 71, p. 2270-2278.

Whitehouse et al. "Electrospray Interface for Liquid Chromatographs and Mass Spectrometers", Anal. Chem. 1985, vol. 57, p. 675-679.

Whitt et al. "Capillary Electrophoresis to Mass Spectrometry Interface Using a Porous Junction", Anal. Chem. 2003, vol. 75, p. 2188-2191.

Yamashita et al. "Electrospray Ion Source. Another Variation on the Free-Jet Theme", J. Phys. Chem. 1984, vol. 88, p. 4451-4459.

Yamashita et al. "Negative Ion Production with the Electrospray Ion Source", J. Phys. Chem. 1984, vol. 88, p. 4671-4675.

Zamfir et al. "Cooper-Coated Microsprayer Interface for on-line Sheathless Capillary Electrophoresis Electrospray Mass Spectrometry of Carbohydrates", J. Sep. Sci. 2006, vol. 29, p. 414-422.

Zhu et al. "A Colloidal Graphite-Coated Emitter for Sheathless Capillary Electrophoresis/Nanoelectrospray Ionization Mass Spectrometry", Anal. Chem. 2002, vol. 74, p. 5405-5409.

English Language Machine Translation of JP06-174693, 8 pgs.

* cited by examiner (a)

(b)

(a)

(b)

(a)

(b)

SELF CONTAINED CAPILLARY ELECTROPHORESIS SYSTEM FOR INTERFACING WITH MASS SPECTROMETRY

CROSS-REFERENCE TO RELATED APPLICATIONS

This application claims the benefit of U.S. provisional application Ser. No. 61/064,485 filed Mar. 7, 2008 and U.S. provisional application Ser. No. 61/193,214 filed Nov. 6, 2008.

FIELD OF THE INVENTION

The present invention relates to a complete capillary electrophoresis (CE) system that is capable of providing a continuous flow of effluent at the exit of the flow-through outlet vial. More particularly, this invention relates to a self-contained capillary electrophoresis system with a flow-through outlet vial for interfacing with mass spectrometry.

BACKGROUND OF THE INVENTION

Capillary electrophoresis (CE) is an analytical technique that uses large electrical potentials applied across narrow bore fused silica capillaries to separate ions in solution. In the applied electrical field, positive and negative ions migrate in solution towards the anode and cathode, respectively. In addition, an electroosmotic flow can also present during the CE processes, depending on the surface charge of the inner capillary wall, the pH, and the electrolyte composition.

Although CE gives excellent separation efficiencies, the small (<100 μm) capillary inner diameters give very short path lengths for optical detection methods. This, along with the small injection volumes used, leads to a concentration sensitivity that is often lower than that achievable using liquid chromatography. One attractive alternative to optical detection is mass spectrometry (MS), which in addition to providing sensitive detection gives additional separation in gas phase and structural information on the analytes. However, interfacing the two methods presents a number of challenges. In order to be analyzed by MS, the ions in solution during CE must be converted to gaseous ions. Additionally, in order to operate in an online fashion the outlet vial of a typical CE instrument must be replaced by another means of electrical contact that does not significantly reduce the separation resolution.

The most popular method to achieve this coupling is electrospray ionization (ESI), which was first proposed as a source of ions for mass analysis. The various teachings of Fenn et al. helped to demonstrate the potential of ESI for mass spectrometry. Since then, ESI has become one of the most commonly used types of ionization techniques due to its versatility, ease of use, and effectiveness for large biomolecules.

ESI involves applying a high electrical potential to a liquid sample flowing through a capillary. Droplets from the liquid sample become charged and an electrophoretic type of charge separation occurs. In positive ion mode ESI, positive ions migrate downstream towards the meniscus of the liquid at the tip of the capillary. Negative ions are repelled back towards the capillary, resulting in charge enrichment. Subsequent fissions or evaporation of the charged droplets result in the formation of single solvated gas phase ions. These ions are then transmitted to the aperture of the mass spectrometer for separation based on their mass to charge ratio and detection.

The challenge in CE-ESI-MS is that both the CE and ESI processes require stable electrical contact of the solution with an electrode at the capillary outlet without interruption of the electroosmotic flow from the CE separation. Many different interfaces have been proposed, however most suffer from issues of excessive sample dilution, loss of resolution, spray instability and/or fragility and cost of the interface. The interfaces proposed for CE-MS can be divided into two categories: those using an additional liquid flow which mixes with the CE eluent, and those which do not.

The first category, known as sheath-flow interfaces, was the most popular type of interface in the early years of CE-MS appplications and is also the design found in current commercial CE-ESI-MS systems. The flowing sheath liquid that surrounds the capillary terminus serves two purposes. The first is to establish electrical contact with the capillary solution in order to drive the CE separation and the ESI process. The second purpose is to modify the composition of the CE electrolyte to make it more compatible with ESI and MS detection. In addition, in the early stages of CE-MS development most interfaces were adapted to fit into existing LC-MS setups, which required much higher flow rates than those delivered by CE. Therefore, the sheath liquid also served to increase the liquid flow to levels comparable to those found in liquid chromatography.

Sheath-flow interfaces also can be further divided into two categories: those where the sheath liquid flow is coaxial with the separation capillary and mixes with the separation buffer at the capillary terminus, and those where the sheath liquid is added by means of a junction before the CE terminus. It has been demonstrated that coaxial sheath flow interfaces give improved performance over those with a liquid junction.

Although sheath-flow interfaces do allow for more diverse conditions to be used during the CE separation, the addition of the sheath liquid dilutes the samples and leads to a significant loss in sensitivity. Because the small injection volumes used in CE give a concentration sensitivity that is low to begin with, this additional loss is in many cases an unacceptable sacrifice. More recently, sheath-flow interfaces have been developed that use even lower flow rates (some less than 200 nL/min) (Wahl, J. H., et al., Attomole Level Capillary Electrophoresis-Mass Spectrometric Protein Analysis Using 5-μm-i.d. Capillaries. Analytical Chemistry, 1992. 64: p. 3194-3196; Olivares, J. A., et al., *On-Line Mass Spectrometric Detection for Capillary Zone Electrophoresis.* Analytical Chemistry, 1987. 59: p. 1231). One of these, the pressurized liquid junction, is similar to the original liquid junction design, however the junction is slightly wider (up to 300 μm) and is located in a pressurized reservoir of make-up liquid. The addition of pressure helps to prevent defocusing of the CE effluent in the gap region that would lead to reduced resolution. To prevent back-flow due to the pressure differential across the separation capillary the inlet vial must also be pressurized. The conductive make-up liquid establishes electrical contact between the background electrolyte (BGE) and the shared electrode, and also supplies a consistent flow to the electrospray tip in cases when the flow rate from CE is insufficient. The additional flow introduced in these 'pressurized junction' interfaces does add a dilution factor, however it is much less than in the case of more traditional sheath-flow interfaces.

A sheath-flow nanospray interface has also been developed using a coaxial arrangement of silica capillaries. The terminal end of the narrow separation capillary is coated with gold to create an electrical contact outside of the separation path. It is then inserted into a larger-diameter silica capillary with the end pulled to a taper. The coaxial capillary assembly is mounted in a standard ionspray interface. Sheath liquid is passed through the larger capillary and flows over the end of the separation capillary, carrying CE effluent to the tapered tip. The dilution factor with this arrangement is less than ½ and the total flow rate of the combined solutions is approximately 500 nL/min.

Another strategy for low volume sheath-flow electrospray interface uses a beveled tip to reduce the required flow rates for stable spray operation without significantly reducing the inner diameter of the emitter tip. One application of the beveled tip uses a novel mixing arrangement that is neither coaxial nor a traditional liquid junction. The CE effluent and sheath liquid are delivered to the emitter tip in parallel capillaries and mixing occurs directly at the emitter orifice.

Despite the dilution that is inherent to sheath-flow interfaces, they offer a number of important advantages. Because the solution exiting the interface is primarily made up of sheath liquid, it is possible to use a wider variety of background electrolytes or additives in the CE process that might otherwise be incompatible with ESI-MS. It is also advantageous to use the sheath-liquid to create electrical contact at the CE capillary terminus, as this keeps the electrolysis process away from the analyte path. Finally, sheath-flow interfaces are generally robust and well suited to commercialization.

Despite recent advances, sheath-flow interfaces have yet to match the sensitivity achievable with sheathless interfaces. Sheathless interfaces are often categorized by the number of pieces through which the liquid flow passes. The first and most common type of sheathless interface involves only a single section of capillary which acts as both the separation channel and the electrospray emitter. In fact, the very first demonstration of mass spectrometry as an online detector for capillary electrophoresis was reported by Olivares and coworkers in 1987 using an interface fabricated by vapour deposition of silver onto a capillary terminus protruding slightly from a metal sheath electrode. The deposited metal created contact between the sheath electrode and the CE electrolyte.

Several other conductive coating materials have been tested in addition to silver, including gold copper, nickel and graphite. Unfortunately coated tips have short lifetimes due to the high electrical fields acting on the metal coating at the tip. Generally they can only be used for a few days before the deterioration of the coating renders operation unstable. Stability may be improved by pre-treating the capillary surface or mixing different materials into the coating.

Peters son and coworkers explored the possibility of using a thin film of static liquid between the capillary tip and a metal sheath pulled back slightly from the capillary tip to establish electrical contact. It has also been demonstrated that CE-ESI-MS can be performed with no electrode whatsoever at the capillary terminus. In this case electrical contact is established through the space between the capillary tip and the grounded orifice of the mass spectrometer. Although this appears to offer an extremely simple solution to interfacing, the position of the capillary tip with respect to the mass spectrometer is critical and it is not possible to control the separation and spray voltages independently.

An alternative to coating the capillary tip is to insert a wire electrode into the capillary channel in order to make electrical contact. Several different means to this end have been tested. When larger inner diameter capillaries are used a thin wire electrode may be inserted into the end of the capillary channel or into a small hole drilled near the capillary terminus. However, this creates turbulence and reduces the resolving power of the CE separation. Turbulence can be reduced by using a hole filled with conductive gold epoxy rather than wire, however, as with any situation where electrolysis occurs within the separation channel this may lead to bubble formation inside the separation channel.

Another strategy for creating electrical contact is to split the liquid flow from the capillary so that a portion of the flow contacts an outside electrode, known as a split-flow interface. Splitting is achieved through a drilled hole or a small crack in a single capillary which serves both as the separation chamber and electrospray tip. While this does well at preserving the separation, the difficulty in this strategy lies in creating reproducible holes or cracks which give the desired split ratio between the two flow paths. An alternative process is the use of hydrofluoric acid to etch away sections of the outside surface of the fused silica capillary to the point where the capillary walls become porous. Electrical contact can then be made through the porous location of capillary wall, either by immersing the etched portion of the capillary in a buffer reservoir, or by inserting it into a metal sheath filled with a thin film of liquid. Although interfaces of this type have been shown to be quite successful, the production is unappealingly hazardous and the capillaries are extremely fragile.

In two-capillary sheathless interfaces, the ends of the separation capillary and a capillary acting as the spray tip are closely butted together at a junction. No additional flow is introduced through the junction however electrical contact is established through a surrounding electrolyte into which the terminal electrode is placed. Junctions have been constructed using microdialysis tubing, a metal sleeve connected to the power source, or a to align the two capillaries and to introduce contact with an electrode. Although these techniques offer the advantage of moving the location of the electrolysis process to the outside of the CE circuit, they are difficult to align in a way that will not decrease the separation resolution. Similarly it is also possible to join the separation capillary with a metal tip that acts as both the sprayer and electrode, however alignment and bubble production remain problematic.

It has been well documented that many organic solvents, salts and other additives commonly used in CE can have a negative impact on the ionization efficiency of analytes of interest. This can be resolved in part by the use of a sheath-flow or liquid-junction interface, which alters the composition of the CE effluent with a more compatible sheath liquid. Similar concepts also exist in liquid chromatography. For example, a modifying solution has been added to LC effluent to counteract the ionization suppression due to trifluoroacetic acid in the mobile phase. Adjustment of this type to the chemical environment of the analytes can significantly increase the detection sensitivity by optimizing ionization conditions.

SUMMARY OF THE INVENTION

An object of one aspect of the present invention is to provide a self-contained capillary electrophoresis system with a flow-through outlet vial for interfacing with mass spectrometry. A further object of the present invention is to provide a means of interfacing capillary electrophoretic and/or chromatographic separations online with detection systems. The detection systems can be one or more of a number of methods for detection and/or analysis, including mass spectrometry analysis. A further object of the present invention is to provide a means of interfacing capillary electrophoretic separations with detection systems which is simple and inexpensive to assemble.

In accordance with an aspect of the present invention there is provided a capillary electrophoresis (CE) microvial coupler for interfacing a capillary with an inline downstream detection system comprising an electrically conductive hollow needle having an inner wall defining an internal tapered chamber, the needle having an upstream opening and a downstream exit orifice, the downstream exit orifice axially opposed to the upstream opening, the internal tapered chamber dimensioned and configured to have a diameter decreasing from a larger diameter at the opening to a smaller diameter at the exit orifice to form a taper on the inner wall in the longitudinal direction from the opening to the exit orifice, the larger diameter at the opening dimensioned and configured to slidably accept a terminus end of a capillary.

In accordance with a further aspect of the present invention there is provided a capillary electrophoresis (CE) system comprising a capillary having an upstream inlet end and a downstream terminus end; an electrically conductive hollow needle having an inner wall defining an internal tapered chamber, the needle having an upstream opening and a downstream exit orifice, the downstream exit orifice axially opposed to the upstream opening, the internal tapered chamber dimensioned and configured to have a diameter decreasing from a larger diameter at the opening to a smaller diameter at the exit orifice to form a taper on the inner wall in the longitudinal direction from the opening to the exit orifice, the larger diameter at the opening dimensioned and configured to slidably accept the terminus end of the capillary, the capillary longitudinally inserted into and mounted within the internal tapered chamber to a distance whereby the terminus end of the capillary abuts the inner wall of the needle at the taper; and wherein a micro-reservoir is formed between the terminus end of the capillary and the downstream exit orifice.

In accordance with another embodiment of the present invention there is provided a sheathless CE-MS interface comprising: an electrically conductive hollow needle having a needle wall defining a chamber tapered along the needle axis from an upstream opening to a downstream orifice; a capillary with an end and an outer diameter, the capillary outer diameter greater than the downstream orifice, the capillary suitable to contain background electrolyte therein, the capillary end disposed within the chamber, the capillary end and the needle wall defining a micro-reservoir; wherein the micro-reservoir is suitable to contain reservoir electrolyte, wherein when the micro-reservoir contains the reservoir electrolyte, the reservoir electrolyte forms an electrical connection between the background electrolyte and the conductive needle to cause CE separation.

In accordance with another embodiment of the present invention there is provided a sheathless CE-MS system comprising: a first vial; an electrode disposed within the first vial; a hollow needle having an electrically conductive wall defining a chamber tapered along the needle axis from an upstream opening to a downstream orifice; a capillary with a first end, a second end, and an outer diameter, the outer diameter greater than the downstream orifice, the first end disposed within the first vial, the second end disposed within the chamber, the second end and the inner wall of the needle defining a micro-reservoir; a counter-electrode adjacent the downstream orifice; a first electrical potential applied between the electrode and the needle; a second electrical potential applied between the needle and the counter-electrode; and wherein the micro-reservoir is suitable to contain reservoir electrolyte, wherein when the micro-reservoir contains the reservoir electrolyte, the reservoir electrolyte forms an electrical connection between the capillary second end and the needle to cause CE separation and electrospray.

Advantages of the present invention include: automatic alignment of the capillary in the tapered needle; a simple and inexpensive interface of capillary electrophoretic separations with detection systems; amenable to mass production; reproducible positioning of the capillary inside the needle in the longitudinal direction; coaxial alignment of the capillary within the needle; designed for ease of replacement of the capillary when required; easily adaptable to auxiliary flow of solution; good resolution of analytes between the separation and electrospray processes.

BRIEF DESCRIPTION OF THE DRAWINGS

A detailed description of the preferred embodiments are provided herein below with reference to the following drawings in which.

Figure 1:
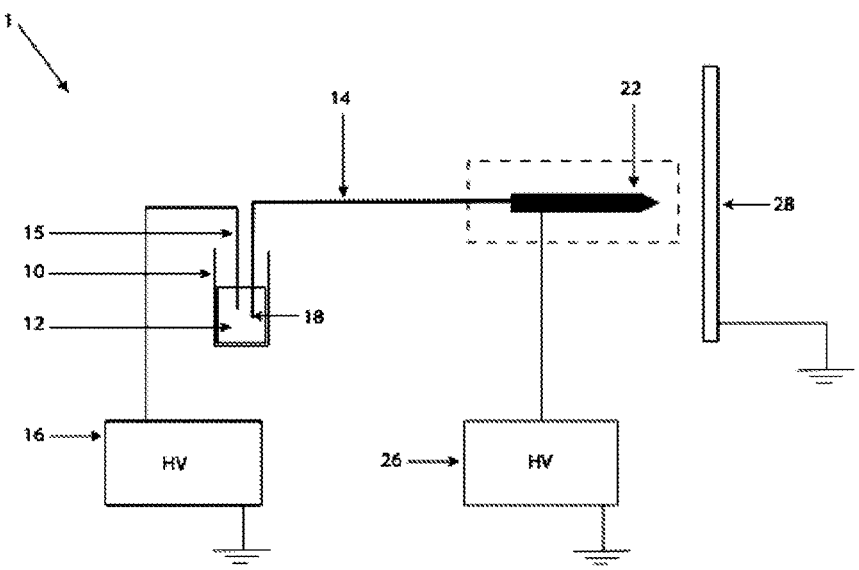
FIG. 1(a), in plan view, illustrates a sheathless capillary electrophoresis-mass spectrometer (CE-MS) system in accordance with an embodiment of the present invention.
FIG. 1(b), in plan view, illustrates in detail the mechanical connection between the capillary, spray needle and fittings of the sheathless CE-MS system of FIG. 1(a).
Figure 1:
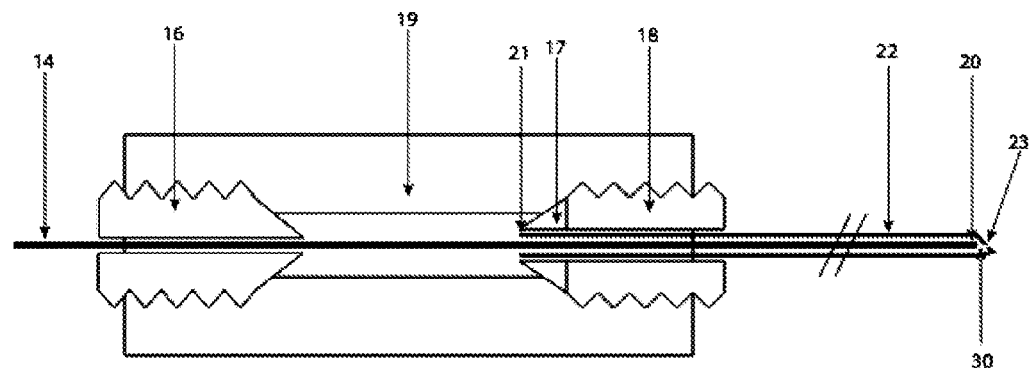

In the drawings, preferred embodiments of the invention are illustrated by way of example. It is to be expressly understood that the description and drawings are only for the purpose of illustration and as an aid to understanding, and are not intended as a definition of the limits of the invention.

DETAILED DESCRIPTION OF THE INVENTION

A separation capillary is inserted into an electro-conductive needle that has an inside diameter slightly larger than the outer diameter of the capillary. At the needle tip the inner geometry of the needle is shaped such that the inner diameter near the tip is less than the outer diameter of the CE separation capillary. For example, the inner geometry of the needle may be tapered or rounded which allows reproducible positioning of the capillary inside the needle in the longitudinal direction since the capillary will only enter the needle to the point where the internal diameter of the needle matches the external diameter of the capillary. Coaxial alignment is also achieved, since the symmetrical internal taper will hold the capillary centred within the needle. The inner diameter of the needle is larger than, equal to, or less than the inner diameter of the capillary. Standard fittings are used to hold the capillary in position, once it has been inserted into the needle. The CE capillary can be easily replaced if necessary, by pulling out the capillary, and inserting a new one. In the case of mass production, single piece CE-MS cartridges, or capillaries with a needle tip attached, can be manufactured at a reasonable cost. A tee union can be used to add an auxiliary flow of solution into the needle, such that the auxiliary solution flows coaxially around the terminus of the separation capillary before exiting the needle.

The open volume at the terminal end of the separation capillary within the sheathless interface constitutes a flow-through micro-reservoir that replaces the outlet vial used in traditional CE separation, providing electrical contact with the electrode, while allowing the analytes and products of electrolysis to pass through to the needle tip. Filling or replenishment of the micro-reservoir may be accomplished simply by flushing the background electrolyte through the CE capillary prior to starting a separation, or by flushing the auxiliary solution through the tee union. The presence of the micro-reservoir volume between the capillary terminus and needle aperture exit does not significantly affect the shapes of peaks separated on the CE capillary. It is therefore possible to maintain good resolution of analytes between the separation and electrospray processes.

The use of this flow-through micro vial essentially decouples the CE process from the interfaced detector, making the CE process less dependent on the type, and the principle of operation, of the coupled detector. The CE process may thus continue regardless of what the detector is. The addition of auxiliary solution can be used to modify both the flow rate and chemical properties of the effluent in order to increase compatibility with subsequent analytical methods. The effluent that comes out of the microvial is then delivered to the next stage process, either by ionization or by other means, to prepare the analyte for the optimized detection condition.

The electrospray needle is connected to a power source and acts as the terminal electrode for the CE separation as well as being part of the electrical circuit necessary for electrospray ionization of the analytes. The relative potentials on the CE inlet electrode, electrospray needle and ESI counter electrode will depend on the modes of CE and ESI desired. In order to compensate for the wide range of flow rates that may be delivered through the use of different CE and modifier conditions, a beveled needle tip can be used. In this case the Taylor cone forms at the sharpest point of the bevel and the size of the cone self-adjusts to the flow rate exiting the needle aperture, allowing for stable spray operation regardless of the flow rate.

Referring to FIGS. 1(*a*) and 1(*b*), there is shown in plan view, a sheathless capillary electrophoresis-mass spectrometer (CE-MS) system (1) in accordance with an embodiment of the present invention. The system (1) comprises a first vial (10) for holding a liquid sample (12); an electrode (15) disposed within the first vial (10) and connected to a first high voltage power supply (16); a fused silica capillary (14) having a first end (18) disposed in the liquid sample (12) and a second end (20). There is provided a electrically conductive hollow needle (22) having an inner wall defining an internal tapered chamber (30) (see FIG. 3(*a*)), the needle (22) having an upstream opening (21) and a downstream exit orifice (23), the downstream exit orifice (23) axially opposed to the upstream opening (21), the internal tapered chamber dimensioned and configured to have a diameter decreasing from a larger diameter at the opening to a smaller diameter at the exit orifice (23) to form a taper on the inner wall in the longitudinal direction from the opening to the exit orifice (23), the larger diameter at the opening dimensioned and configured to slidably accept the second end (20) of the capillary (14). As illustrated in FIG. 1(*b*), standard chromatography fittings including upstream and downstream PEEK or stainless steel nuts (16, 18), a union (19) and a ferrule (17) are provided to connect and hold the capillary (14) and the needle (22) in place. The needle (22) is connected to a second power supply (26) so that a first electrical potential can be applied between the electrode (15) and the needle (22). A counter electrode (28) is positioned downstream of the exit orifice (23) of the needle (22). The counter electrode (28) may be any standard mass spectrometry sample aperture, or any instrumental interface that is electrically connected. The relative voltages on the first vial (10), needle (22) and counter electrode (28) will depend on the mode of capillary electrophoresis and electrospray ionization desired. The region between the exit orifice (23) of the needle (22) and the counter electrode (28) may be held at atmospheric pressure.

Figure 3:
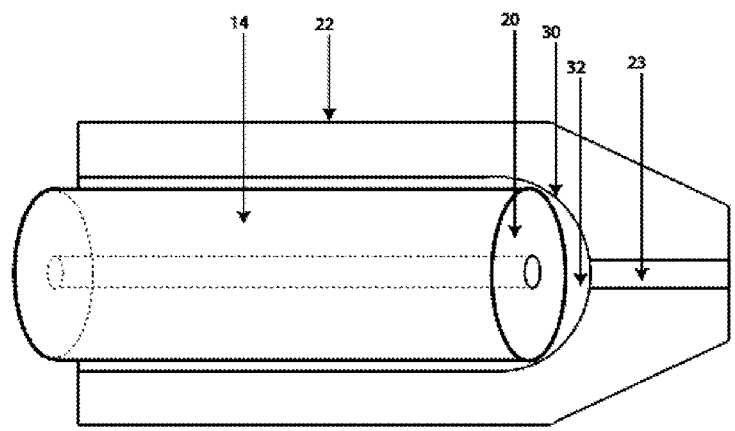
FIG. 3(a), in plan view, illustrates in detail the insertion of the separation capillary into the electrospray needle of the sheathless CE-MS system of FIG. 1.
FIG. 3(b), in plan view, illustrates in detail the insertion of the separation capillary into the electrospray needle of the sheathless CE-MS system of FIG. 2.
Figure 3:
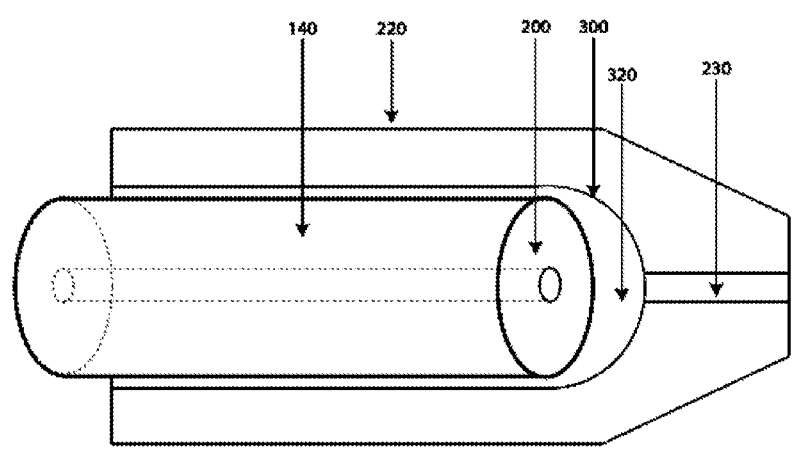

As shown in FIG. 3(*a*), when the second end (20) of the capillary (14) is inserted into the internal tapered chamber (30) of the needle (22) a flow-through micro-reservoir (32) is formed between the second end (20) of the capillary (14) and the downstream exit orifice (23). The micro-reservoir (32) is suitable to contain reservoir electrolyte, wherein when the micro-reservoir (32) contains the reservoir electrolyte, the reservoir electrolyte forms an electrical connection between the second end (20) of the capillary (14) and the needle (22) to cause capillary electrophoresis separation and electrospray. The micro-reservoir may take many shapes in addition to the ones depicted in FIG. 3 and, in an extreme case, may simply be the volume of the needle aperture and the thickness of the metal at the tip of the electrode. A feature of the micro-reservoir is that it provides electrical contact between the metal spray needle and the solution within the capillary.

Figure 2:
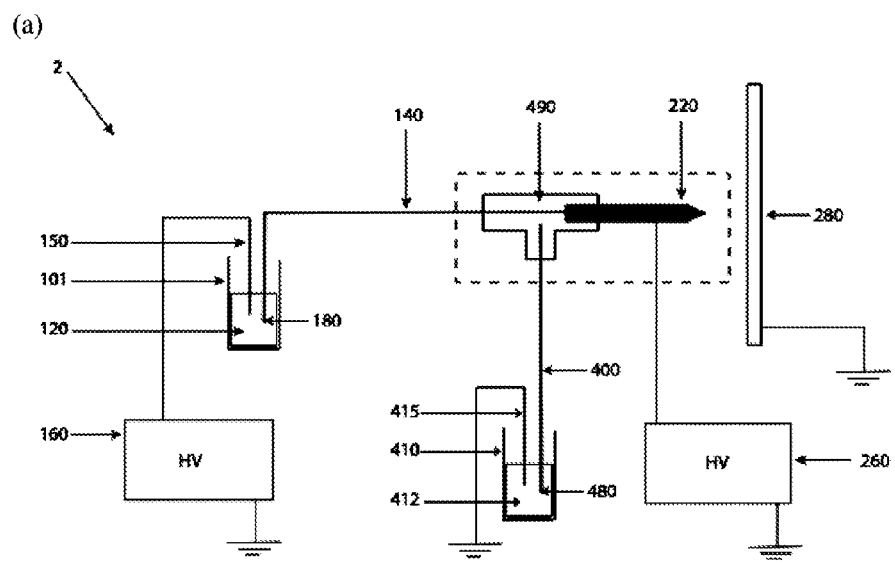
FIG. 2(a), in plan view, illustrates a sheathless CE-MS system in accordance with another embodiment of the present invention.
FIG. 2(b) in plan view, illustrates in detail the mechanical connection between the capillary, spray needle and fittings of the sheathless CE-MS system of FIG. 2(a)
Figure 2:
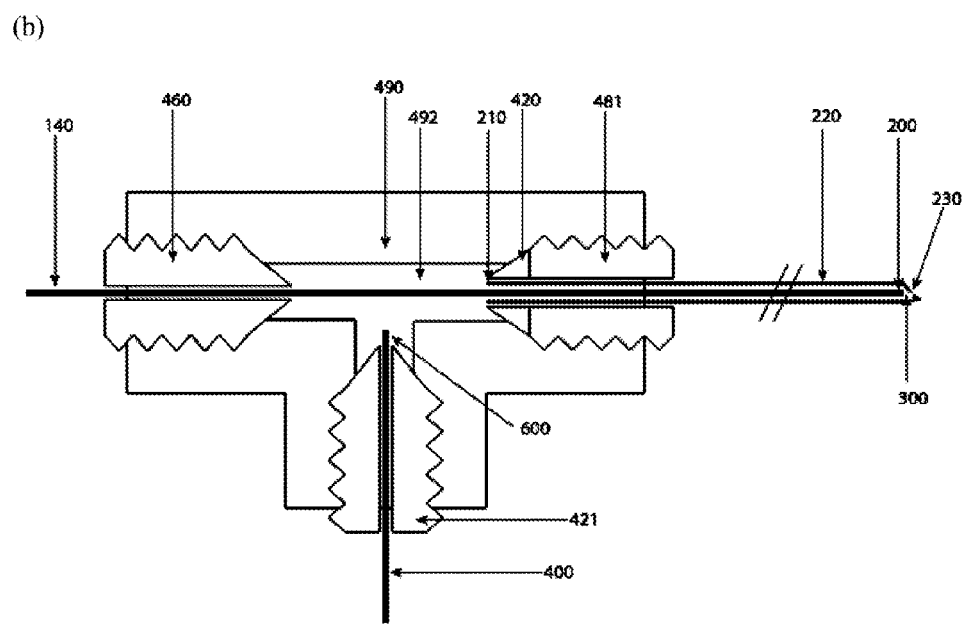

Referring to FIGS. 2(*a*) and 2(*b*), there is shown in plan view, a sheathless capillary electrophoresis-mass spectrometer (CE-MS) system (100) in accordance with another embodiment of the present invention. The system (100) comprises a first vial (101) for holding a liquid sample (120); an electrode (150) disposed within the first vial (101) and connected to a first high voltage power supply (160); a first fused silica capillary (140) having a first end (180) disposed in the liquid sample (120) and a second end (200). There is provided a electrically conductive hollow needle (220) having an inner wall defining an internal tapered chamber (300) (see FIG. 3(*b*)), the needle (220) having an upstream opening (210) and a downstream exit orifice (230), the downstream exit orifice (230) axially opposed to the upstream opening (210), the internal tapered chamber dimensioned and configured to have a diameter decreasing from a larger diameter at the opening to a smaller diameter at the exit orifice (230) to form a taper on the inner wall in the longitudinal direction from the opening to the exit orifice (230), the larger diameter at the opening dimensioned and configured to slidably accept the second end (200) of the first capillary (140). The system (100) further comprises an auxiliary fused silica capillary (400) having a first end (480) and a second end (600). The first end (480) disposed in an auxiliary liquid sample (412) contained in an auxiliary vial (410), an auxiliary electrode (415) disposed within the auxiliary vial (410) and connected to ground.

As illustrated in FIG. 2(b), standard chromatography fittings including upstream and downstream PEEK or stainless steel nuts (460, 481), a tee junction (490), a ferrule (420) and a PEEK nut (421), are provided to connect and hold the first capillary (140) and the needle (220) in place in a linear alignment and to hold and orient the auxiliary capillary (400) perpendicularly therebetween. The needle (220) is connected to a second power supply (260) so that a first electrical potential can be applied between the electrode (150) and the needle (220). A counter electrode (280) is positioned downstream of the exit orifice (230) of the needle (220). The counter electrode (280) may be any standard mass spectrometry sample aperture, or any instrumental interface that is electrically connected. The relative voltages on the first vial (101), needle (220) and counter electrode (280) will depend on the mode of capillary electrophoresis and electrospray ionization desired. The region between the exit orifice (230) of the needle (220) and the counter electrode (280) may be held at atmospheric pressure.

As shown in FIG. 3(b), when the second end (200) of the first capillary (140) is inserted into the internal tapered chamber (300) of the needle (220) a flow-through micro-reservoir (320) is formed between the second end (200) of the capillary (140) and the downstream exit orifice (230). The micro-reservoir (320) is suitable to contain reservoir electrolyte, wherein when the micro-reservoir (320) contains the reservoir electrolyte, the reservoir electrolyte forms an electrical connection between the second end (200) of the first capillary (140) and the needle (220) to cause capillary electrophoresis separation and electrospray.

Auxiliary liquid sample (412) flows through the auxiliary capillary (400) from the first end (480) to the second end (600) and into the internal chamber (492) of the tee junction (490) thereby surrounding the outer surface of the first capillary (140) and flowing into the micro-reservoir (320).

FIG. 3 demonstrates the self-aligning properties of the present invention, whereby the internal taper of the spray needle guides the capillary to a position that is both centred with respect to the needle exit orifice and consistent with respect to the volume of the micro-reservoir.

The micro-reservoir offers the unique feature that the interface provides a complete outlet vial substitute, such that CE can be performed in the absence of an electrospray.

Figure 4:
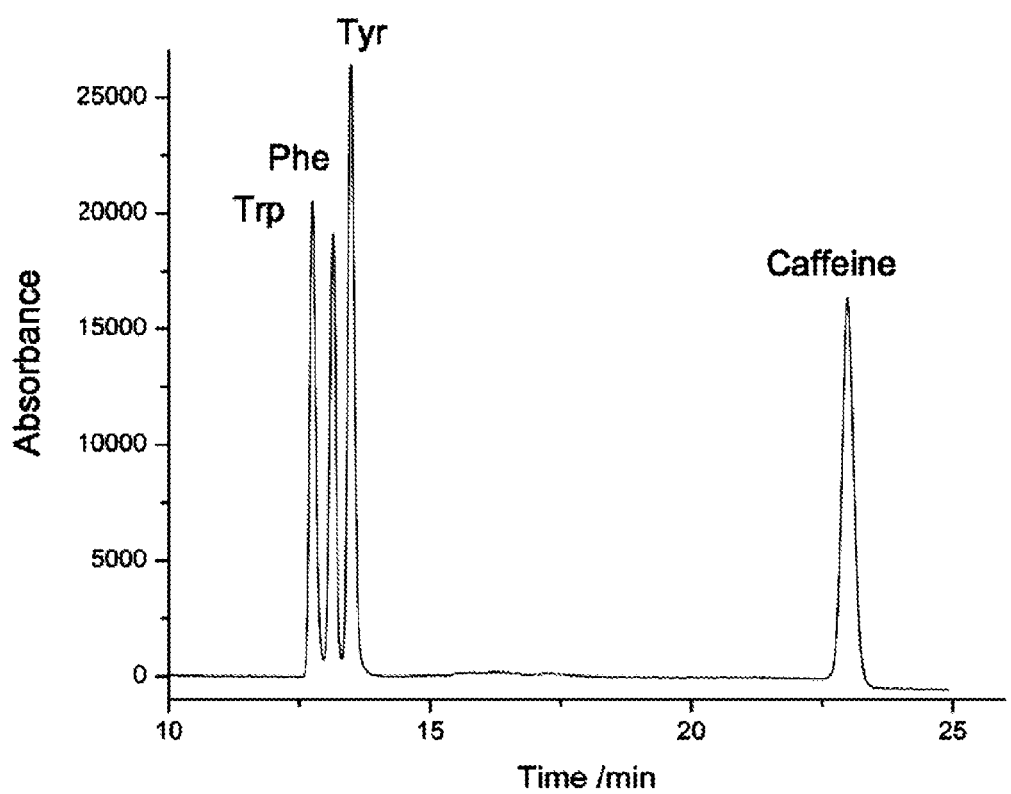
FIG. 4 illustrates an exemplary absorbance trace of an electrophoretic separation obtained using an embodiment of the present invention operating in CE-only mode.

Referring to FIG. 4 there is illustrated an exemplary absorbance trace of an electrophoretic separation obtained using an embodiment of the present invention operating in CE-only mode. FIG. 4 shows the absorbance trace of the separation of a mixture of amino acids and caffeine using the interface in CE-only mode. In this case the needle is grounded and liquid exits the needle as drops. The CE-only mode offers improved versatility, allowing the use of electrokinetic injection prior to CE separation without altering the CE-MS set-up. It also makes available the possibility of only spraying for a part of the CE separation, which would be advantageous for online focusing or derivitization techniques requiring high-salt buffers or surfactants.

Figure 5:
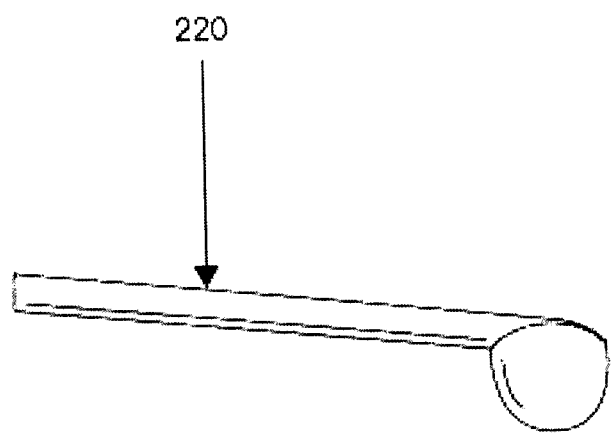
FIG. 5 illustrates an exemplary liquid drop exiting the electrospray needle of an embodiment of the invention when operated in CE-only mode.

Referring to FIG. 5, there is illustrated an exemplary liquid drop exiting the electrospray needle of an embodiment of the invention when operated in CE-only mode.

Figure 6:
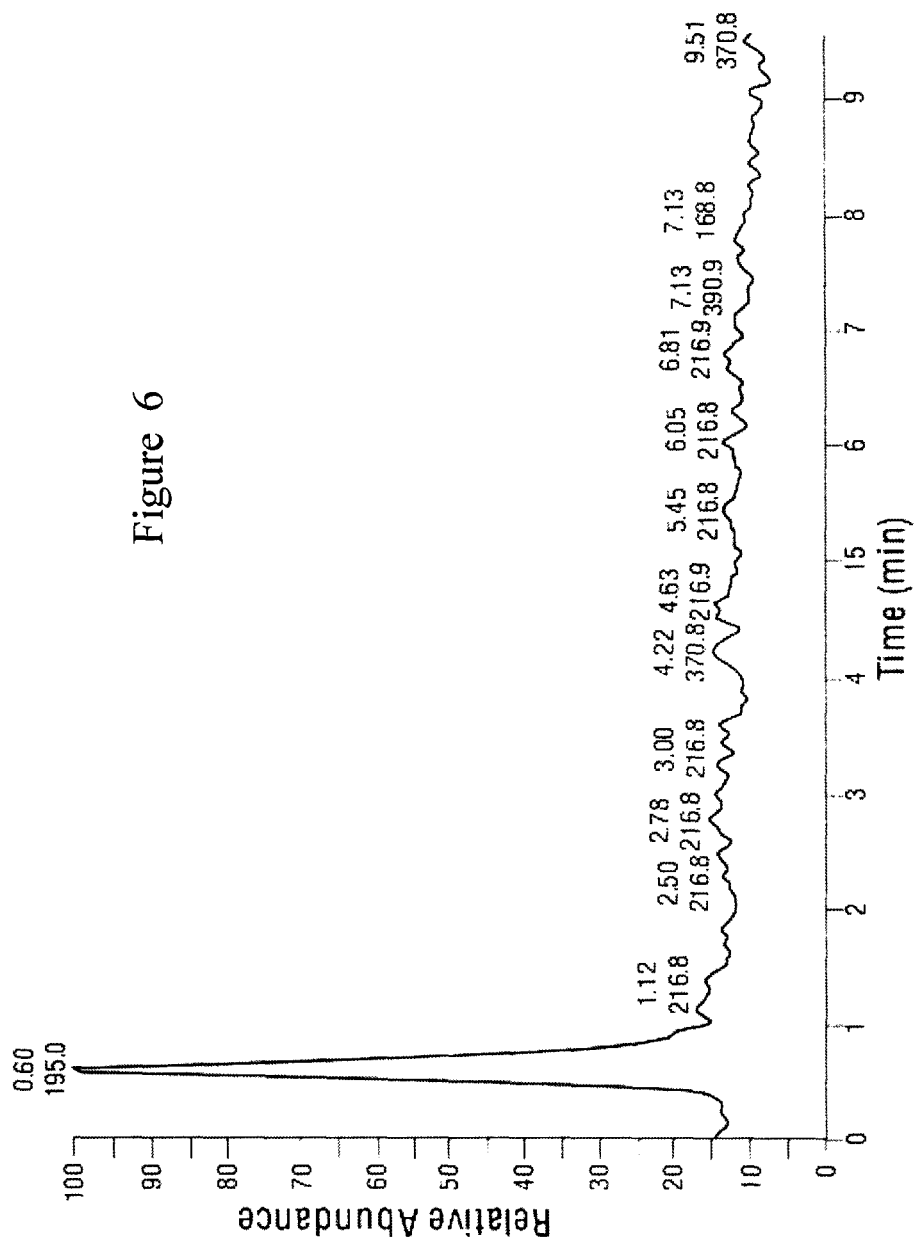
FIG. 6 illustrates an exemplary mass spectral trace obtained from an embodiment of the invention set for operation as an electrospray ionization source only.

Referring to FIG. 6, there is illustrated an exemplary mass spectral trace obtained from an embodiment of the invention set for operation as an electrospray ionization source only. FIG. 6 shows the interface operating in ESI-only mode without auxiliary solution. A plug of caffeine (0.5 mM in phosphate, pH 9, 10% methanol) is sprayed and detected by MS as it is pushed through the interface using pressure only. The injection was run at 25 kV for 0.5 s at 10 psig. The symmetric peak profile shows that the solution in the micro reservoir and the shape of the micro vial does not distort the peak shape significantly, and that the analyte coming out of the capillary is not trapped by the micro reservoir.

Figure 7:
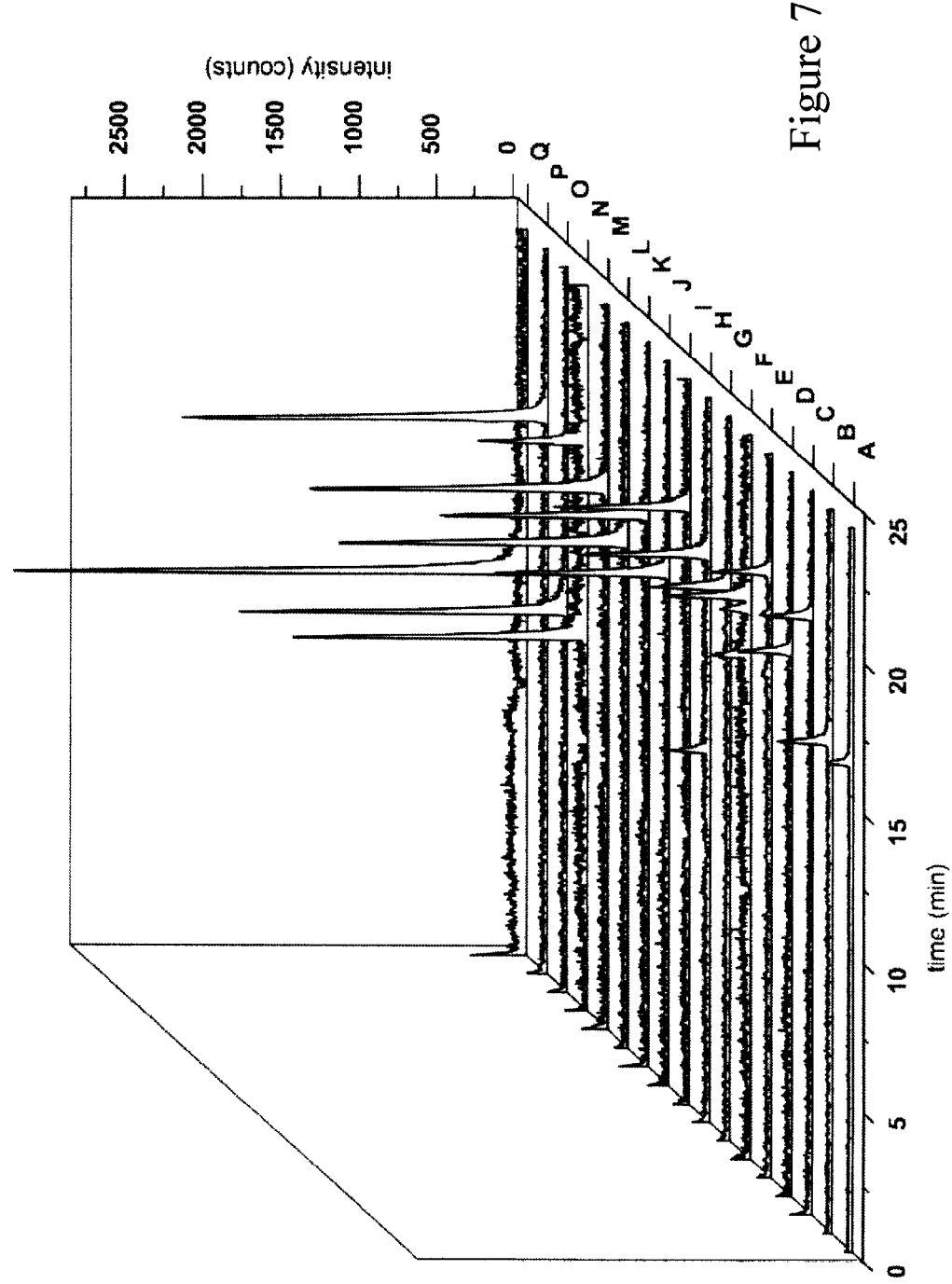
FIG. 7 illustrates exemplary mass spectral data obtained from operation of an embodiment of the invention for separation of a mixture of amino acids. The amino acid electropherograms are A) Glycine, B) Alanine, C) Serine, Proline, E) Valine, F) Threonine, G) Cysteine, H) Isoleucine, I) Asparagine, J) Aspartic acid, K) glutamine, Lysine, L) Glutamic acid, M) Methionine, N) Histidine, O) Phenylalanine, P) Arginine, Q) Tryptophan.

Referring to FIG. 7 there is illustrated exemplary mass spectral data obtained from operation of an embodiment of the invention. FIG. 7 shows the mass spectral data for a CE separation of a mixture of amino acids with the use of an auxiliary flow to compensate for the near-zero bulk flow of the CE separation when an acidic background electrolyte is used. A mixture of amino acids is separated by CE and separated by the MS. The separation of the amino acids A) Glycine, B) Alanine, C) Serine, D) Proline, E) Valine, F) Threonine, G) Cysteine, H) Isoleucine, I) Asparagine, J) Aspartic acid, K) glutamine, Lysine, L) Glutamic acid, M) Methionine, N) Histidine, O) Phenylalanine, P) Arginine, Q) Tryptophan is illustrated.

Figure 8:
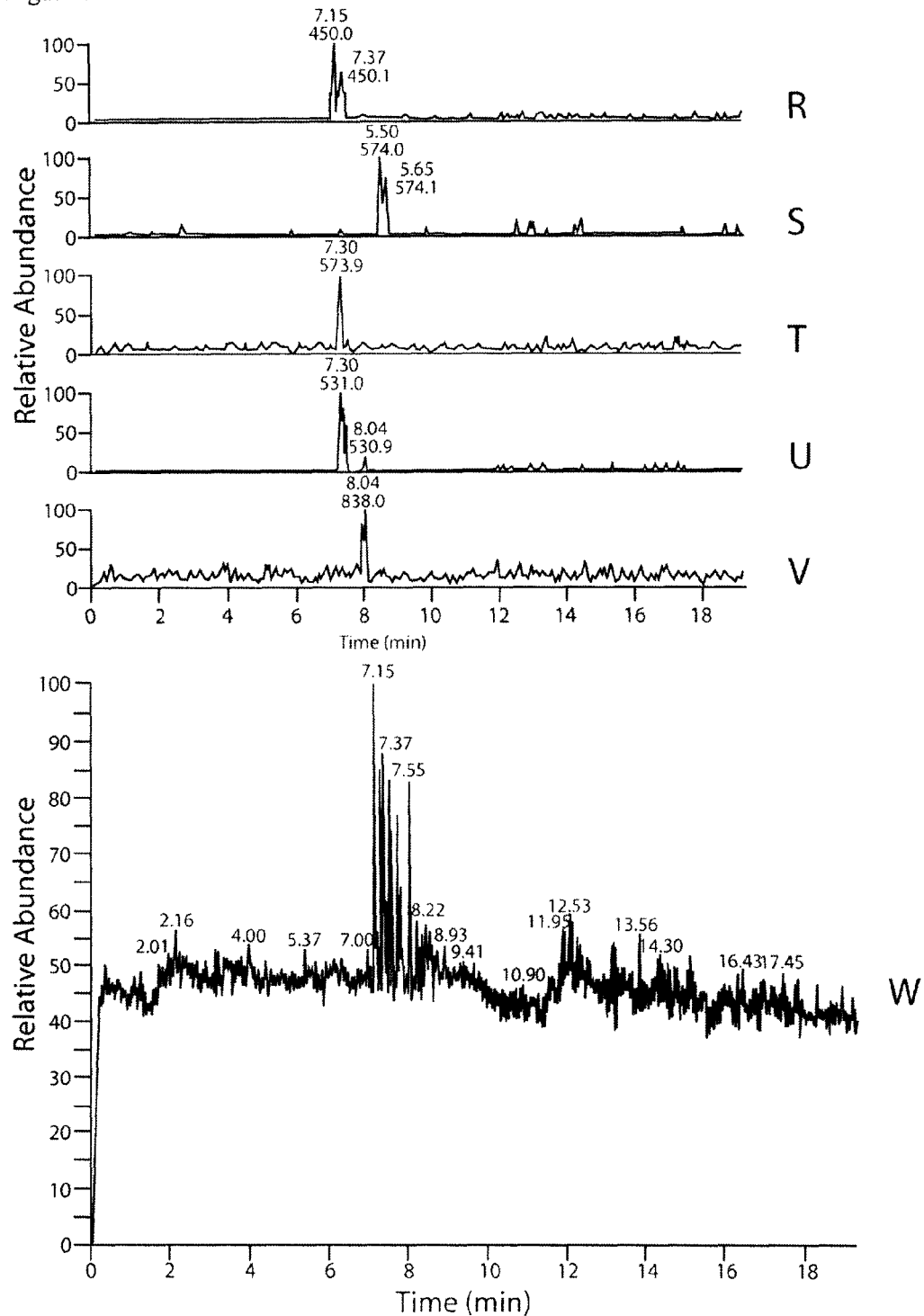
FIG. 8 illustrates exemplary mass spectral data for separation of a mixture of peptides using an embodiment of the present invention. The electropherograms are identified as corresponding to R) Angiotensin II (+2); S) Met Enkaphalin (+1), T) Substance P (+2), U) Bradykinin (+2), V) Neurotensin (+2), and W) total ion.

Referring to FIG. 8 there is illustrated the mass spectral data for a pressure-assisted CE separation of a mixture of five peptides with online electrospray ionization. W illustrates the total ion electropherogram. R is identified as the electropherogram for Angiotensin II (+2) with a m/z range of 449.6-450.3. S is identified as the electropherogram for Met Enkaphalin (+1) with a m/z range of 573.8-574.2. T is identified as the electropherogram for Substance P (+2) with a m/z range of 672.9-674.4. U is identified as the electropherogram for Bradykinin (+2) with a m/z range of 530.0-531.1. V is identified as the electropherogram for Neurotensin (+2) with a m/z range of 837.5-838.8. Neither the CE separation parameters nor the electrospray parameters were optimized prior to the analysis. The peak identities for the various charge states of the peptides analyzed are recorded in Table 1 below.

TABLE 1

Separation of a mixture of 5 peptides

| peptide | charge: | | | | |
|---|---|---|---|---|---|
| | +1 | +2 | +3 | +4 | +5 |
| | Peak (m/z) | | | | |
| angiotensin II | 895.88 | 896.9 | 448.9 | 299.6 | 225.0 | 180.2 |
| neurotensin | 1671.66 | 1672.7 | 836.8 | 558.2 | 418.9 | 335.3 |
| bradykinin | 1058.76 | 1059.8 | 530.4 | 353.9 | 265.7 | 212.8 |
| met enkephalin | 572.7 | 573.7 | 287.4 | 191.9 | 144.2 | 115.5 |
| substance P | 1345.7 | 1346.7 | 673.9 | 449.6 | 337.4 | 270.1 |

Figure 9:
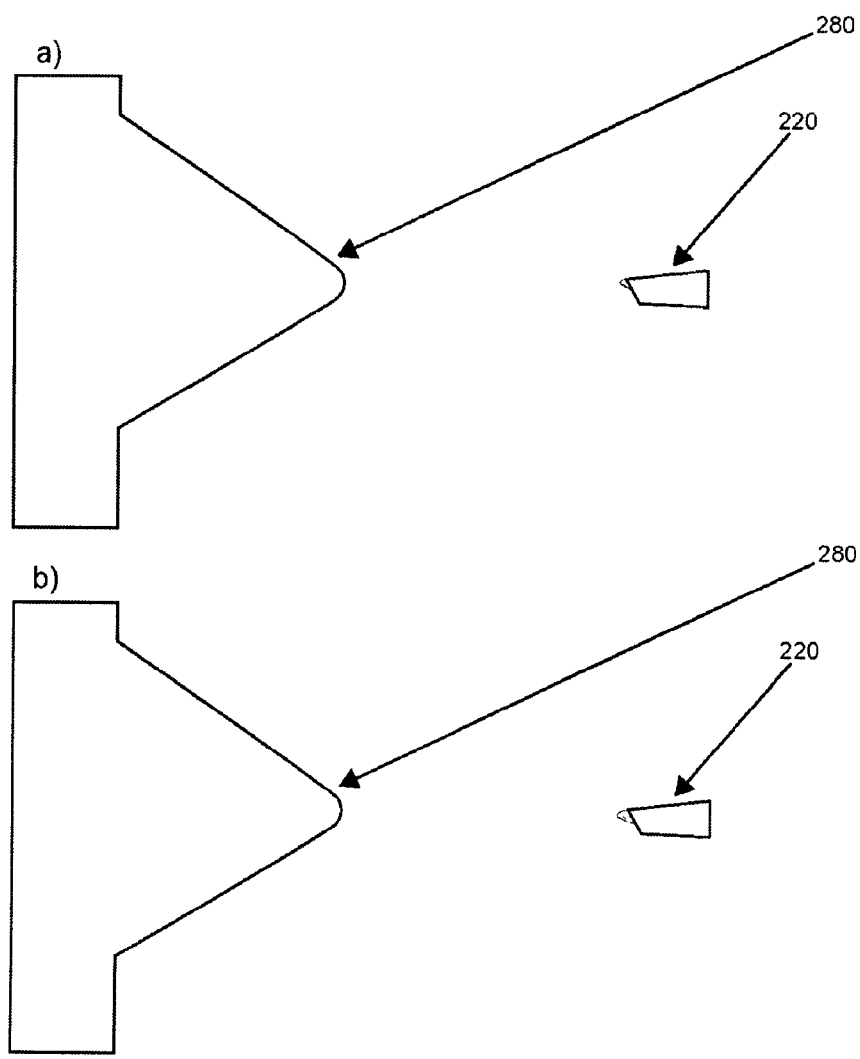
FIG. 9 illustrates electrospray ionization occurring from a needle having a beveled tip of an embodiment of the present invention at (a) high and (b) low flow rates.

Referring to FIG. 9, there is illustrated exemplary electrospray ionization occurring from a beveled needle tip with a beveled tip at (a) high and (b) low flow rates. The self-adjusting properties of the Taylor cone in response to different flow rates can be observed. In 9 (a) a modifier is added at a low flow rate, leading to the formation of a small Taylor cone at the sharpest point of the bevel. In 9 (b) the modifier flow rate is increased and the size of the Taylor cone increases correspondingly. This demonstrates the self-adjusting properties of the interface when used with a beveled needle tip. A larger range of effluent flow rate can be handled by the same interface without any additional modification of the system.

Numerous modifications, variations, and adaptations may be made to the particular embodiments of the invention described above without departing from the scope of the invention. All such modifications or variations are believed to be within the sphere and scope of the invention as defined by the claims appended hereto.

What is claimed is:

1. A column separation system comprising:
   a capillary having an upstream inlet end and a downstream terminus end;
   an electrically conductive hollow needle having an inner wall defining an internal tapered chamber, the needle having an upstream opening and a downstream exit orifice, the downstream exit orifice axially opposed to the upstream opening, the internal tapered chamber dimensioned and configured to have a diameter decreasing from a larger diameter at the opening to a smaller diameter at the exit orifice to form a taper on the inner wall in a longitudinal direction from the opening to the exit orifice, the larger diameter at the opening dimensioned and configured to slidably accept the terminus end of the capillary, the capillary longitudinally inserted into and mounted within the internal tapered chamber to a distance whereby the terminus end of the capillary in operational state abuts the inner wall of the needle at the taper; and
   a flow-through micro-reservoir is formed between the terminus end of the capillary and the downstream exit orifice.

2. The system of claim 1 further comprising:
   a junction means upstream of the needle for providing an auxiliary solution whereby the auxiliary solution is directed to flow coaxially along the outside of the capillary from the upstream opening of the needle to the flow-through micro-reservoir.

3. The system of claim 2 wherein the junction means further comprises
   a tubular body portion having a first opening and a second opening, the first opening axially opposed to the second opening, the tubular body portion dimensioned and configured to allow passage of the capillary therethrough;
   a means for securing the capillary in the first opening;
   a means for securing the needle in the second opening; and
   a tubular branch portion having a branch opening, the tubular branch portion being in fluid communication with the tubular body portion via the branch opening located between the first opening and the second opening of the tubular body portion, the tubular branch portion provided with means for securing an auxiliary capillary within the branch opening.

4. The system of claim 3 wherein the column separation system is a capillary electrophoresis system and the downstream exit orifice of the needle is adapted for use as an electrospray emitter, the electrospray emitter is coupled to a mass spectrometer, the needle has a downstream bevel shaped tip, and the internal tapered chamber of the needle has a parabolic shape, the parabolic shape having a smaller diameter at the downstream exit orifice of the needle and a larger diameter at the opening of the internal tapered chamber.

5. The system of claim 1 wherein the downstream exit orifice of the needle is adapted for use as an electrospray emitter.

6. The system of claim 1 wherein the downstream exit orifice of the needle is coupled to a mass spectrometer.

7. The system of claim 1 wherein the downstream exit orifice of the needle is coupled to a fraction collection apparatus.

8. The system of claim 1 wherein the downstream exit orifice of the needle is coupled to an external analytical apparatus.

9. The system of claim 1 wherein the column separation system is a capillary electrophoresis system.

10. The system of claim 1 wherein the downstream exit orifice of the needle is adapted for use as an electrospray emitter and the electrospray emitter is coupled to a mass spectrometer.

11. The system of claim 1 wherein,
    the needle has a downstream bevel shaped tip; and
    the internal tapered chamber of the needle has a parabolic shape, the parabolic shape having a smaller diameter at the downstream exit orifice of the needle and a larger diameter at the opening of the internal tapered chamber.

12. The system of claim 11 wherein the downstream exit orifice of the needle is adapted for use as an electrospray emitter.

13. The system of claim 1 wherein the column separation system which is a capillary electrophoresis system and wherein the downstream exit orifice of the needle is adapted for use as an electrospray emitter and the electrospray emitter is coupled to a mass spectrometer.

14. The system of claim 13 wherein the internal tapered chamber of the needle has a parabolic shape, the parabolic shape having a smaller diameter at the downstream exit orifice of the needle and a larger diameter at the opening of the internal tapered chamber.

15. The system of claim 1 wherein the column separation system is a capillary electrophoresis system and the downstream exit orifice of the needle is adapted for use as an electrospray emitter, the electrospray emitter is coupled to a mass spectrometer, the needle has a downstream bevel shaped tip, and the internal tapered chamber of the needle has a parabolic shape, the parabolic shape having a smaller diameter at the downstream exit orifice of the needle and a larger diameter at the opening of the internal tapered chamber.

16. The system of claim 1 wherein the needle has a downstream bevel shaped tip.

17. The system of claim 1 wherein the internal tapered chamber of the needle has a parabolic shape, the parabolic shape having a smaller diameter at the downstream exit orifice of the needle and a larger diameter at the opening of the internal tapered chamber.

18. A capillary electrophoresis-mass spectrometer system comprising:
    a first vial;
    an electrode disposed within the first vial;
    an electrically conductive hollow needle having an inner wall defining an internal tapered chamber, the needle having an upstream opening and a downstream orifice, the downstream orifice axially opposed to the upstream opening, the internal tapered chamber dimensioned and configured to have a diameter decreasing from a larger diameter at the upstream opening to a smaller diameter at the downstream orifice to form a taper on the inner wall in a longitudinal direction from the upstream opening to the downstream orifice;
    a capillary with a first end, a second end, and an outer diameter, the outer diameter greater than the downstream orifice, the first end disposed within the first vial, the second end disposed within the internal tapered chamber, wherein the larger diameter at the opening of the needle is dimensioned and configured to slidably accept the second end of the capillary, the second end of the capillary in operational state abuts the inner wall of the needle at the taper, the second end and the inner wall of the needle defining a flow-through micro-reservoir, the flow-through micro-reservoir suitable to contain reservoir electrolyte, wherein when the flow-through micro-reservoir contains the reservoir electrolyte, the reservoir electrolyte forms an electrical connection between the capillary second end and the needle, and when a first electrical potential is applied between the electrode and the needle, capillary electrophoresis separation is effected;

a counter-electrode adjacent the downstream orifice, wherein when the flow-through micro-reservoir contains the reservoir electrolyte; and a second electrical potential is applied between the needle and the counter-electrode, electrospray ionization is effected downstream of the flow-through micro-reservoir, thereby separating the capillary electrophoresis separation and the electrospray ionization.

19. The capillary electrophoresis-mass spectrometer system of claim 18 wherein the needle has a beveled tip.

20. The capillary electrophoresis-mass spectrometer system of claim 19 wherein the internal tapered chamber of the needle has a parabolic shape, the parabolic shape having a smaller diameter at the downstream orifice of the needle and a larger diameter at the opening of the internal tapered chamber.

21. The capillary electrophoresis-mass spectrometer system of claim 18 further comprising a second vial or other fluid reservoir in fluid communication with the upstream opening of the needle wherein the second vial or other fluid reservoir is pressurized and wherein the second vial or other fluid reservoir provides the reservoir electrolyte.

22. The capillary electrophoresis-mass spectrometer system of claim 18 wherein the first vial is pressurized and wherein the first vial provides the reservoir electrolyte.

23. The capillary electrophoresis-mass spectrometer system of claim 18 further comprising a junction means upstream of the needle for providing an auxiliary solution whereby the auxiliary solution is directed to flow coaxially along the outside of the capillary from the upstream opening of the needle to the flow-through micro-reservoir.

24. The capillary electrophoresis-mass spectrometer system of claim 23 wherein the junction means further comprises
  a tubular body portion having a first opening and a second opening, the first opening axially opposed to the second opening, the tubular body portion dimensioned and configured to allow passage of the capillary therethrough;
  a means for securing the capillary in the first opening;
  a means for securing the needle in the second opening; and
  a tubular branch portion having a branch opening, the tubular branch portion being in fluid communication with the tubular body portion via the branch opening located between the first opening and the second opening of the tubular body portion, the tubular branch portion provided with means for securing an auxiliary capillary within the branch opening.

25. The capillary electrophoresis-mass spectrometer system of claim 24 wherein the needle has a beveled tip and the internal tapered chamber of the needle has a parabolic shape, the parabolic shape having a smaller diameter at the downstream orifice of the needle and a larger diameter at the opening of the internal tapered chamber.

26. The capillary electrophoresis-mass spectrometer system of claim 18 wherein the internal tapered chamber of the needle has a parabolic shape, the parabolic shape having a smaller diameter at the downstream orifice of the needle and a larger diameter at the opening of the internal tapered chamber.

27. The capillary electrophoresis-mass spectrometer system of claim 18 further comprising a second vial or other fluid reservoir in fluid communication with the upstream opening of the needle wherein the second vial or other fluid reservoir is pressurized, and,
  the first vial is pressurized; and
  the first vial and the second vial or other fluid reservoir provide the reservoir electrolyte.

28. The capillary electrophoresis-mass spectrometer system of claim 18 further comprising a second vial or other fluid reservoir in fluid communication with the upstream opening of the needle wherein the second vial or other fluid reservoir is pressurized, and,
  the needle has a beveled tip;
  the internal tapered chamber of the needle has a parabolic shape, the parabolic shape having a smaller diameter at the downstream orifice of the needle and a larger diameter at the opening of the internal tapered chamber;
  the first vial is pressurized; and
  the first vial and the second vial or other fluid reservoir provide the reservoir electrolyte.

29. An interface for coupling a column separation system with an inline downstream detection system, the interface comprising:
  an electrically conductive hollow needle having an inner wall defining an internal tapered chamber, the needle having an upstream opening and a downstream orifice, the downstream orifice axially opposed to the upstream opening, the internal tapered chamber dimensioned and configured to have a diameter decreasing from a larger diameter at the opening to a smaller diameter at the downstream orifice to form a taper on the inner wall in a longitudinal direction from the upstream opening to the downstream orifice; and
  a capillary having an upstream inlet end, a downstream terminus end and an outer diameter, a capillary outer diameter being greater than the downstream orifice,
  the larger diameter at the opening of the needle is dimensioned and configured to slidably accept the end of the capillary, and in operational state the capillary longitudinally inserted into and mounted within the internal tapered chamber to a distance whereby the terminus end of the capillary abuts the inner wall of the needle at the taper, and
  a flow-through micro-reservoir is formed between the terminus end of the capillary and the downstream orifice.

30. The interface of claim 29 wherein the needle has a beveled tip asymmetric about a needle axis.

31. The interface of claim 29 wherein the internal tapered chamber of the needle has a parabolic shape, the parabolic shape having a smaller diameter at the downstream orifice of the needle and a larger diameter at the opening of the internal tapered chamber.

32. The interface of claim 29 wherein,
  the needle has a beveled tip asymmetric about a needle axis; and
  the internal tapered chamber of the needle has a parabolic shape, the parabolic shape having a smaller diameter at the downstream orifice of the needle and a larger diameter at the opening of the internal tapered chamber.

33. The interface of claim 32 wherein the downstream orifice of the needle is adapted for use as an electrospray emitter.

34. The interface of claim 33 wherein the interface couples a capillary electrophoresis system with a mass spectrometer.

35. The interface of claim 29 wherein the column separation system is selected from a group consisting of a capillary electrophoresis system, nano-liquid chromatography system, ultra-high pressure microcolumn liquid chromatography system and capillary electrokinetic chromatography system, and wherein the inline downstream detection system is selected from the group consisting of a mass spectrometer, fraction collection apparatus, external analytical apparatus and capillary flow-injection system.

36. The interface of claim 35 wherein,
   the needle has a beveled tip asymmetric about a needle axis; and
   the internal tapered chamber of the needle has a parabolic shape, the parabolic shape having a smaller diameter at the downstream orifice of the needle and a larger diameter at the opening of the internal tapered chamber.

37. The interface of claim 29 wherein the interface couples a capillary electrophoresis system with a mass spectrometer.

38. The interface of claim 37 wherein the capillary is suitable to contain background electrolyte therein and the flow-through micro-reservoir is suitable to contain reservoir electrolyte, and wherein when the flow-through micro-reservoir contains the reservoir electrolyte, the reservoir electrolyte forms an electrical connection between the background electrolyte and the conductive needle to cause capillary electrophoresis separation.

39. The interface of claim 38 wherein the reservoir electrolyte is provided through the capillary.

40. The interface of claim 38 wherein the reservoir electrolyte is provided through the upstream opening of the needle.

41. The interface of claim 38 wherein the reservoir electrolyte is provided through the capillary and through the upstream opening of the needle.

42. The interface of claim 38 wherein,
   the downstream orifice of the needle is adapted for use as an electrospray emitter;
   the needle has a beveled tip asymmetric about a needle axis;
   the internal tapered chamber of the needle has a parabolic shape, the parabolic shape having a smaller diameter at the downstream orifice of the needle and a larger diameter at the opening of the internal tapered chamber; and
   the reservoir electrolyte is provided through the capillary and through the upstream opening of the needle.

43. The interface of claim 29 wherein the downstream orifice of the needle is adapted for use as an electrospray emitter.

44. The interface of claim 43 wherein the interface couples a capillary electrophoresis system with a mass spectrometer.

* * * * *